United States Patent
Kawasaki et al.

(10) Patent No.: US 7,834,326 B2
(45) Date of Patent: Nov. 16, 2010

(54) ABERRATION CORRECTOR AND CHARGED PARTICLE BEAM APPARATUS USING THE SAME

(75) Inventors: Takeshi Kawasaki, Musashino (JP); Noboru Moriya, Tokorozawa (JP); Tomonori Nakano, Kokubunji (JP); Kotoko Hirose, Abiko (JP)

(73) Assignee: Hitachi High-Technologies Corporation, Tokyo (JP)

( * ) Notice: Subject to any disclaimer, the term of this patent is extended or adjusted under 35 U.S.C. 154(b) by 254 days.

(21) Appl. No.: 12/187,635

(22) Filed: Aug. 7, 2008

(65) Prior Publication Data

US 2009/0039281 A1    Feb. 12, 2009

(30) Foreign Application Priority Data

Aug. 8, 2007    (JP) .............................. 2007-206655

(51) Int. Cl.
*H01J 1/50*    (2006.01)
(52) U.S. Cl. .......................... 250/396 ML; 250/396 R; 250/492.3; 250/311; 250/310
(58) Field of Classification Search ................. 250/306, 250/307, 310, 311, 396 R, 396 ML, 492.1, 250/492.3

See application file for complete search history.

(56) References Cited

U.S. PATENT DOCUMENTS

| | | | |
|---|---|---|---|
| 5,041,731 A | 8/1991 | Oae et al. | |
| 6,946,663 B2 | 9/2005 | Kawai | |
| 7,211,804 B2 | 5/2007 | Yoshida et al. | |
| 2007/0125954 A1* | 6/2007 | Frosien ................... | 250/396 R |

FOREIGN PATENT DOCUMENTS

| | | |
|---|---|---|
| JP | 2001-312988 | 11/2001 |
| JP | 2004-234961 | 8/2004 |
| JP | 2004-241190 | 8/2004 |

OTHER PUBLICATIONS

H. Rose, et al, Optik 22, (1971), pp. 1-24.
Zach, et al, "Aberration Correction in a Low Voltage SEM by a Multipole Corrector", Nuclear Instruments and Methods in Physics Research A 363 (1995) 316-325.

* cited by examiner

*Primary Examiner*—Jack I Berman
*Assistant Examiner*—Michael Maskell
(74) *Attorney, Agent, or Firm*—Mattingly & Malur, P.C.

(57) ABSTRACT

The present invention provides an aberration corrector giving excellent assembly accuracy but having fewer parts and fewer adjustment locations in number. In order to achieve it, a multistage multipole is formed by arranging plural combinations of electrodes around an optical axis using alignment blocks, each combination of electrodes being made by brazing-integrating plural electrodes with a ceramic material interposed therebetween.

16 Claims, 7 Drawing Sheets

ABERRATION CORRECTOR AND CHARGED PARTICLE BEAM APPARATUS USING THE SAME

CLAIM OF PRIORITY

The present invention claims priority from Japanese patent application JP 2007-206655, filed on Aug. 8, 2007, the content of which is hereby incorporated by reference into this application.

BACKGROUND OF THE INVENTION

The present invention relates to a structure of an aberration corrector used for a charged particle beam apparatus, and a charged particle beam apparatus equipped with the aberration corrector.

In the charged particle beam apparatuses, such as the scanning electron microscope, the scanning transmission electron microscope, the transmission electron microscope, and the focused ion beam machining system, multipole (dipole, quadrupole, octapole, etc.) have been used for the deflector and the astigmatism corrector. In recent years, in order to correct spherical aberration and chromatic aberration of an objective lens with axially rotational symmetry, the aberration corrector made by combining the quadrupole, hexapole, octapole, etc. has been proposed and developed. Actually in 1995, it was shown by Haider et al. that the spherical aberration can be corrected in the TEM, and it was shown by Zach et al. that the chromatic aberration and the spherical aberration can be corrected in the SEM (for example, see H. Rose, Optik 33 (1971) pp. 1-24 and J. Zach and M. Haider, Nuclear Instruments and Methods in Physical Research, A363 (1995) pp. 316-325). In these aberration correctors, it is required that a multipole field that is a high-precision superposition of fields is formed in an area through which a charged particle beam passes. As means for actually implementing such a multipole field, there is no method except arranging multipole for forming the multipole field on the same axis so as to be in a multistage structure at present. Therefore, all the aberration correctors currently manufactured have a configuration where multipoles are arranged in a multistage structure.

The conventional multipole mainly include: the magnetic field type multi-magnetic pole that is intended to be used in the spherical aberration correctors for TEM and STEM, the EELS apparatus, etc.; the electrostatic type multipole that is used for electrostatic deflection in the SEM, the electron beam lithography system, etc. and the electrostatic-magnetic field superposition type multipole for chromatic and spherical aberration corrector. Magnetic poles do not need to be exposed in a vacuum passage of the charged particle beam, whereas in the electrostatic type or electromagnetic multipole, poles need to be exposed, and therefore the latter is sensitive to dirt and protrusions on the surface of poles. Moreover, the electromagnetic multipole needs to have a complicated configuration, such as a fact that each pole is insulated from other poles electrically and each pole is connected magnetically to the other poles with a yoke, so that electromagnetic poles constitute a magnetic circuit. What is commonly required for these is excellent accuracy in assembling the multipoles, capability for generating a multipole field with sufficient symmetry, and high-precision coincidence of a mechanical axis of an upper multipole and a lower multipole, and a phase around the axis when a multistage configuration is adopted. From a viewpoint of mass productivity, it is mentioned that parts and adjustment locations are fewer in number and an adjustment work is simple. However, at present, a manufacture method for manufacturing the aberration corrector that satisfies both mass productivity and the assembly accuracy has not been established.

JP-A-2004-234961 discloses a magnetic multipole such that a yoke for connecting a magnetic pole and a magnetic pole is integrated into a single piece by wire electrical discharge machining. Moreover, this patent document (JP-A-2004-234961) shows 1) an electrode aligning and fixing method by plural pins, and 2) electrode aligning and fixing method using a high-precision cylinder. Moreover, JP-A-2004-241190 discloses a method for manufacturing multipole by fixing uncut multipole with a screw, and after that cutting the uncut portion.

SUMMARY OF THE INVENTION

In the manufacturing process of an aberration corrector, not only manufacturing a multipole with high precision for each stage but also assembling plural multipoles with high precision is required. Although the each patent document described above discloses a technology of machining one stage of multipole with high precision, it discloses no technology of assembling manufactured multipoles in a stage direction with high precision.

For example, the electrical discharge machining method disclosed in JP-A-2004-234961 allows very high-precision manufacture of the multipole if considering manufacture of only one stage of the multipole (or multi-magnetic pole). However, when applying the electrical discharge machining method to collective formation of the multistage of multipoles, adjusting the inclination of the wire to become straight to an optical axis becomes difficult as the number of stages becomes large (that is, the multistage becomes long in the optical axis direction). Therefore, it is difficult to maintain machining accuracy of unevenness of the multipole to a necessary level (typically, about ±5 μm in parallel to the optical axis). If the machining accuracy of about ±5 μm is not maintainable, unnecessary parasitic aberration will occur and performance of the aberration corrector will be deteriorated.

Moreover, by the method disclosed by JP-A-2004-241190, when an uncut multipole is fixed to the fixed stand with a screw, a force is imposed on the material and distorts the tip of the multipole; therefore, re-machining of the tip of the multipole becomes necessary after cutting the uncut portion. Although it is thought that the re-machining itself is realizable, for example, by wire electrical discharge machining etc., it takes much time to do washing of electrical discharge machining liquid, etc. Moreover, the electrode cutting and shaping after magnetic annealing may cause a change in the magnetic property of the magnetic pole, and accordingly there is a possibility that the magnetic field becomes asymmetry.

Furthermore, the collective formation method of multipole, as disclosed by JP-A-2004-234961 and JP-A-2004-241190, comes with a problem that modification machining in case machining defect etc. occurs is troublesome. If the shape of the tip of the pole changes by re-machining, it is necessary to fine adjust the gap between the multipoles and their positions according to the change of the shape. However, in the manufacturing method whereby the multipole is formed collectively, it is impossible to perform fine adjustment of the gap of the tip of the electrode and their positions on an electrode basis, and if the modification machining becomes needed, the machining of the multipole must be redone from the beginning after all.

Therefore, in the present invention, the following conditions are given: 1) the mechanical axis and phases around the axis of the multipoles are adjusted to one another with high precision, 2) the number of parts and the number of adjustment locations are smaller than that of the conventional case, an assembly work is simple, and the aberration corrector is suited to mass production.

Realizing the aberration corrector using the multipoles that has the above features and a charged particle beam apparatus using the aberration corrector has been set as problems.

In the above-mentioned aberration corrector, two or more electrodes are integrated and these are assembled to the multistage multipoles. In the subsequent explanation, such an integrated electrodes will be called a "multipole element." In the present invention, a configuration where electrodes are arranged around the optical axis of a charged particle optical system is realized by attaching plural multipole elements to a fixed base. In manufacturing the multipole element, the plural electrodes are integrated by an insulating material. Electrodes are made into a single piece by bonding these electrodes in a vertical direction with an insulating material interposed therebetween. This is because the multipoles constituting the multistage multipoles need to be insulated mutually in the stage direction. As the insulating material, ceramic materials such as alumina and zirconia are suitable. As a method for bonding upper and lower electrodes, there are techniques, such as brazing, adhesion, mechanical junction, and diffusion welding. The bonding by brazing is most suitable from reasons that the brazing gives strength endurable to grinding and the brazing is suitable for use in a vacuum. In the spherical aberration corrector for TEM and STEM, only magnetic multipoles are used, which does not need insulation principally. However, the method of fixing the magnetic pole to the base in high accuracy can be used by common.

According to the present invention, since a multistage multipole is assembled using the multipole element as a building block, both the number of parts necessary for the assembly and the number of assembly steps are reduced compared to the conventional technology whereby the multistage multipole is assembled using the electrode as a building block. Moreover, since the multipole is assembled not by making the whole multipoles into a single piece but by using the building block of the multipole element, arrangement of the multipole element in an in-plane direction can be adjusted freely. That is, the present invention has an advantage that it is very easy to perform position adjustment of an electrode tip and fine adjustment of a gap between electrodes at the time of reworking the electrodes. Moreover, an interval of multipole in a stage direction can be set with excellent accuracy by grinding.

Since the multistage multipole can be simply assembled with high accuracy according to the present invention, the present invention can provide the aberration corrector suited to mass production and its application apparatus.

DETAILED DESCRIPTION OF THE PREFERRED EMBODIMENTS

Figure 1A:
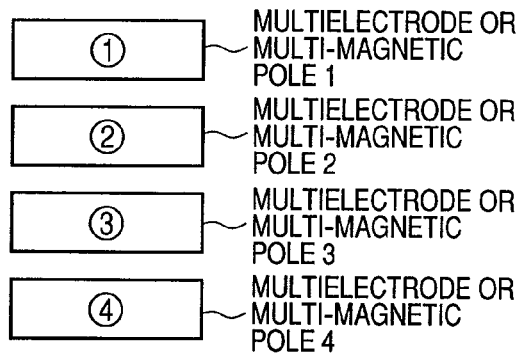
FIGS. 1(A) to 1(E) are schematic diagrams showing a concept of multistage multipoles of the present invention.
Figure 1B:
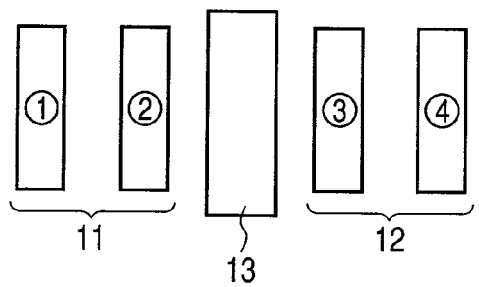
Figure 1C:
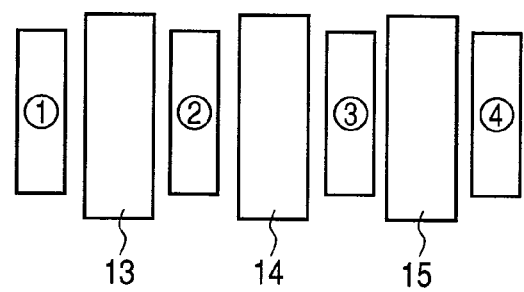

Using FIGS. 1(A) to 1(E), the most fundamental configuration and the operation and effect of the present invention will be described. As one example of an aberration corrector constructed with the multistage multipole, FIG. 1(A) shows a schematic diagram of a cross section of a four-stage multipole. It should be understood that this four-stage multipoles is constructed using a multipole element of the present invention. The number of stages of the multipole element is assumed to be two stages for simplification. In the case where the four-stage multipole shown in FIG. 1(A) is constructed using two multipole elements, the simplest configuration would be such that two multipole elements 11, 12 as shown in FIG. 1(B) are attached to the both sides of a single fixed base 13. For comparison, FIG. 1(C) shows a schematic diagram of a cross section in the case where the four-stage multipole is constructed by the conventional assembly method that does not use the multipole element. Here, considering the number of times of attachment of the multipole to the fixed bases 13 to 15 in the assembly process of the four-stage multipole shown in FIG. 1(B) and FIG. 1(C), in the case of FIG. 1(B), the number of times of attachment is total two: a sum of one on the front face of the fixed base 13 and one on the rear face. On the other hand, in the case of FIG. 1(C), since the three support bases 13, 14, and 15 are used as fixed bases, the number of times of attaching the multipoles thereto is two times to the front face and the rear face of the each fixed base, being six times in total. Since attaching the multipole to the fixed base is necessarily accompanied with position adjustment between the electrodes, the multistage multipole of the structure shown in FIG. 1(B) allows the number of times of position adjustment between the electrodes to be one third that of the multistage multipole of the structure shown in FIG. 1(C).

As described above, construction of the multistage multipole using the building block of the multipole element makes it possible to substantially reduce the number of times of position adjustment of the electrodes in the multipole plane and in the stage direction.

Figure 1D:
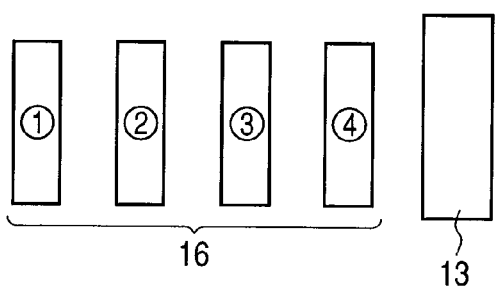
Figure 1E:
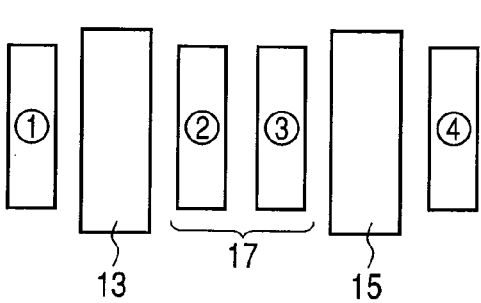

FIG. 1(D) is a schematic diagram showing a sectional structure of the four-stage multipole in the case where the multipole is specified to have four stages of the multipole elements. In this case, the number of times of attachment of a four multipole element 16 (four-stage accumulated multipole) to the fixed base is one time, which shows the number of times of attachment to the fixed base is reduced to one sixth that of FIG. 1(C) that is the conventional technology, being even reduced to one half that of FIG. 1(B). FIG. 1(E) shows a cross section of the four-stage multipole in the case where only two stages of a midsection of the four-stage multipole are specified as the multipole element. In this case, although the number of times of attachment is four, being increased above those of the configurations of FIG. 1(B) and FIG. 1(D), the number of times of attachment can be reduced below that of the configuration by the conventional technology.

As described above, the most fundamental configuration of the present invention lies in that when configuring the multistage multipole, at least two stages of them are constructed with the multipole element. Adopting such a configuration reduces the number of times of attachment to be less than the conventional number, which makes it easy to configure the multipole in the form of a multistage. Therefore, the number of times of position adjustment of the electrodes can be reduced below the conventional number, and it becomes an excellent method in mass production of multistage multipoles.

First Embodiment

Figure 2A:
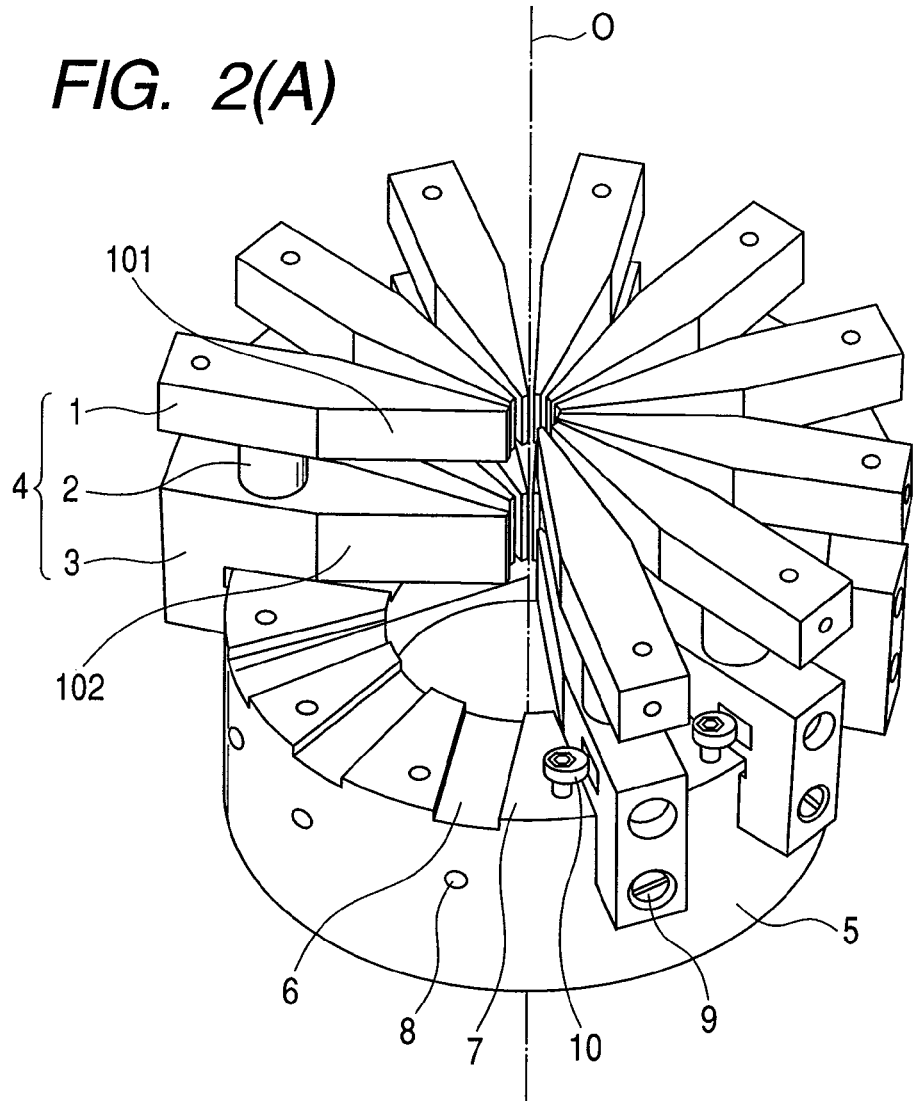
FIGS. 2(A) and 2(B) are schematic diagrams of a two-stage 12-electrode to which the present invention is applied.
Figure 2B:
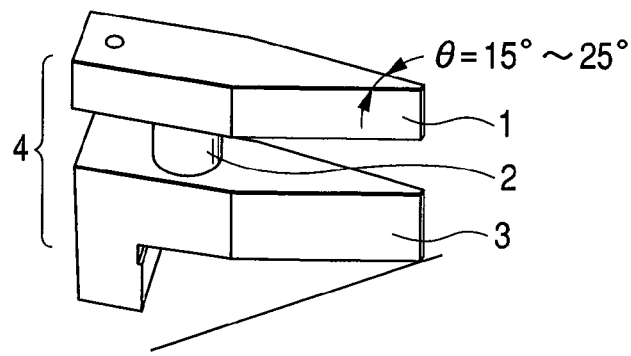

In this embodiment, an embodiment will be explained in which the multipole element made by bonding the electrode and the magnetic pole in upper and lower two stages, a two-stage multipole is constructed using the electromagnetic multipole element, and the aberration corrector is constructed using the two-stage multipole elements. FIG. 2(A) shows an example of a two-stage dodecapole that is constructed using 12 multipole elements shown in FIG. 2(B). The multipole element shown in FIG. 2(B) is equivalent to a multipole element in which the two electrodes 11 of FIG. 1(B) has been fixed to the fixed base 13.

An electrode 1 obtained by cutting a non-magnetic metal (titanium etc.) whose thermal expansion rate is comparatively small into a predetermined shape is brazed to an electrode or magnetic pole 3 obtained by cutting a soft magnetic metal (Permalloy etc.) into a predetermined shape via an alumina prop 2 using silver braze, and so the above members 1, 2, and 3 constitute a single piece of a multipole element 4. Since the alumina prop has sufficient strength and bonding method is brazing, so that the bonding strength is attained sufficiently, the multipole element 4 does not bend toward the optical axis because of its weight. In the case of this embodiment, the electrode 1 corresponds to an electrode, and the electrode or magnetic pole 3 corresponds to a magnetic pole. By fixing 12 multipole elements to a support base 5, a two-stage dodecapole lens of an electromagnetic field superposition type can be formed. In order to constitute 4 stage chromatic and spherical aberration corrector, it is necessary to attach further a two-stage 12-electrode to a rear face of the support base 5.

After formation of the multipole element 4, slight grinding processing is performed on side faces, a top face, and an underface of the multipole element to equalize angles of a wedge shape 101 and a wedge shape 102. Since the upper and lower electrodes can be subjected to collective finish machining as the multipole element, perpendicularity between the electrodes 1, 3 and shapes of electrode tips can be finished with micrometer accuracy. Moreover, since the finish machining is done on a one-by-one basis of the multipole element, the number of steps of the finish machining is reduced and a total time required for the machining is shortened compared to the conventional multipole manufacture method where the finish machining is performed for each of the electrodes, one by one.

After the finish machining, 12 multipole elements are arranged around the charged electron beam optical axis 0 by fixing them to the support base 5. Twelve grooves 6 are formed so as to guide the electrode or magnetic pole 3 in the support base 5. One-sided sidewalls among two-sided sidewalls of the grooves are considered as base level 7 of angles of the electrodes, and have been machined by accurately adjusting rotation angles in a direction perpendicular to the optical axis. Locating of the electrode is done by pressing the multipole element toward the support base center along this base level and the electrode is fixed with a fixed screw. A hole 8 designates a screw hole into which a fixed screw 9 is screwed. A decentering screw 10 is provided on the top face of the support base 5. The decentering screw 10 presses the electrode 3 to the base level 7 and at the same time presses it so that it may not rise from the groove bottom plane. This action prevents a play of the electrode or magnetic pole 3 in the circumferential direction. As described above, by performing groove machining on the top face or the underface of the support base and thereby providing the pressing base level, the two-stage multipole such that the attachment of the electrode to around the optical axis is easier than the conventional method and disposition accuracy of the tip of the electrode is also high can be realized. In forming the four-stage multipole, a groove that is the same as that of the top face of the support base 5 is machined on the rear face and the two-stage multipole is attached to the groove.

Making multistages that is equal to or more than four-stages can be realized either by combining plural support bases or by combining the multipole elements each of which has the number of electrodes in the vertical direction increased to three or more.

In the conventional method for fixing the electrode using plural locating pins (a method as disclosed in the conventional art paragraphs in JP-A-2004-234961), in order to attain accuracy of order of micrometer, it is necessary to repeat fine adjustment of eccentricity of the locating pins while measuring a position of a tip of the electrode with an electric micrometer, a three-dimensional measurement device, etc. Therefore, its assembly requires skilled workmanship of a level of master performance, and therefore has the remotest possibility of becoming a manufacture technique with mass productivity. In the manufacture method of this embodiment in which a fixing groove and the pressing base level are provided on the support base surface, the assembly accuracy is determined by both machining accuracy of the electrode and machining accuracy of the support base, and there is no position that an assembly person should adjust while performing measurement. Therefore, the assembly of the multipole can easily be done only by fastening machine screws being accurately, and the multipole excellent in assembly reproductivity can be constructed. Moreover, the assembly of this multipole requires a fewer number of parts than the conventional multipole that requires locating pins and fixing pins for each electrode, and the assembly process itself of the multipole is simplified. Furthermore, since this multipole allows fewer holes to be drilled through the electrodes compared to the pinning method etc., when using the magnetic poles, there is less disorder of the magnetic field inside the magnetic poles, and the cross section of the magnetic pole can be enlarged, becoming less prone to cause magnetic saturation.

Incidentally, there is a case where the dodecapole is intended to be used to form a dipole field, quadrupole field, hexapole field, and an octapole field to correct parasitic aberration. In that case, an arbitrary electrode field is generated by connecting power supplies independent for respective electrodes to the electrodes necessary to constitute the respective multipole among 12 electrodes. For example, in the case of the 12-electrode of this embodiment, a formation field of each of the dipole (deflector), the quadrupole, the hexapole, the octapole, and dodecapole and superposition fields thereof (electric field or magnetic field) can be formed. Especially, in the case where the dipole field, quadrupole field, the hexapole field, and octapole field are formed with the 12-magnetic pole, if all the magnetic poles take the same form of an arrow among them, intense multi-magnetic pole fields whose aperture diameters are small can be formed. However, if a gap between itself and the adjacent magnetic pole is narrow in a wedge slope part, the magnetic field will not concentrate on the center and leaks to the adjacent one. In the case of the hexapole field, a result of simulation revealed that if the tip angle of the wedge is set to 15°, the six-electrode field whose strength is about two times that of 30° is generated. If the wedge angle is too acute, machining will become difficult. From a practical point of view, it is preferable that the tip angle of the 12-magnetic pole is 15° to 25°.

Figure 3:
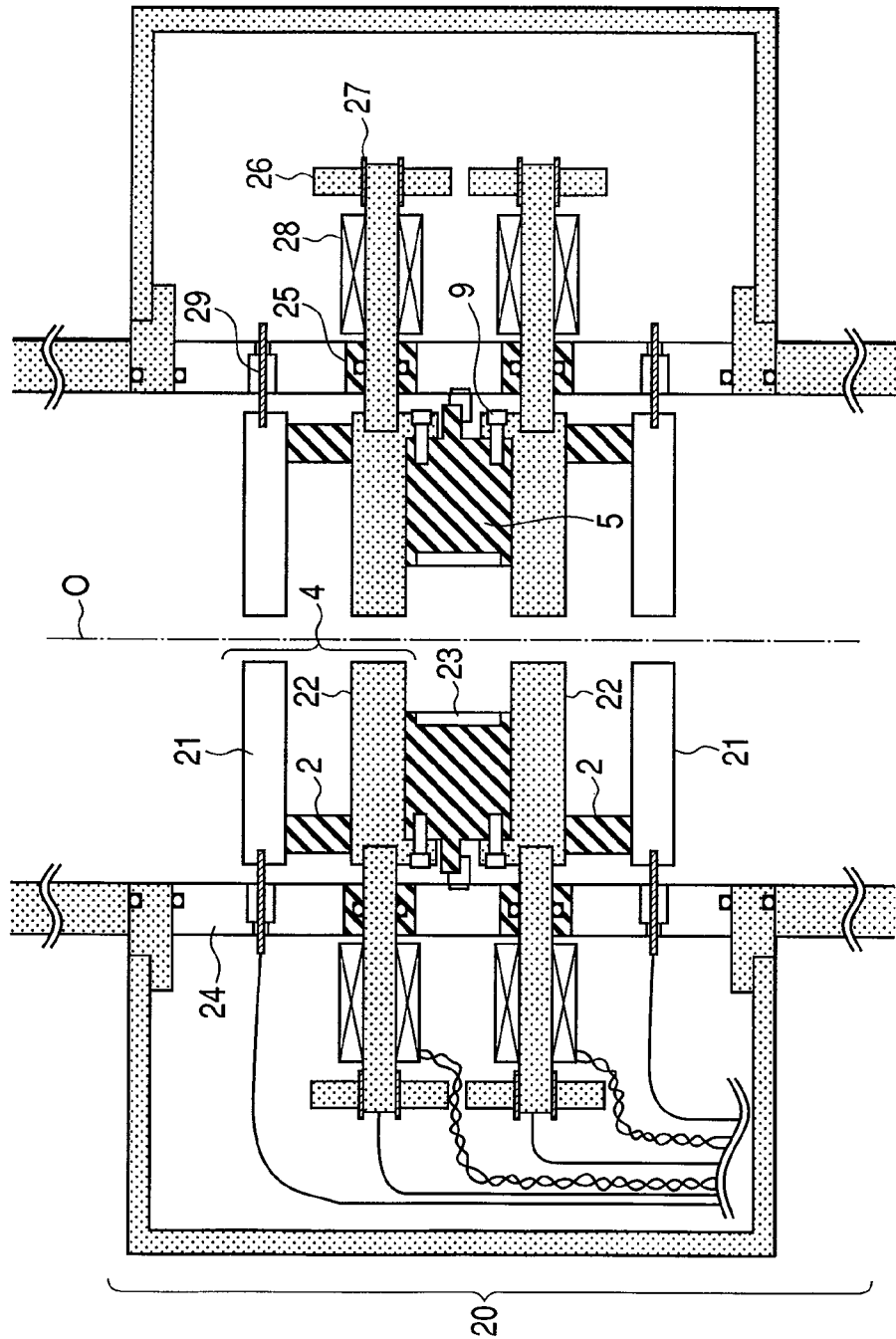
FIG. 3 is an outline configuration of a four-stage chromatic and spherical aberration corrector to which the present invention is applied.

Next, a configuration example of the aberration corrector using the multipole shown in FIGS. 2(A) and 2(B) will be explained. FIG. 3 shows a configuration example of a four-stage 12-electrode aberration corrector capable of correcting chromatic aberration and spherical aberration. This aberration corrector has a configuration where two sets of the two-stage 12-electrode shown in FIGS. 2(A) and 2(B) are arranged symmetrically in a vertical direction with a support base of an insulator material interposed therebetween. The first stage and the fourth stage are electric field type dodecapoles. An electrode 21 that constitutes the dodecapole is made up of a titanium. The second stage and the third stage are electromagnetic field superposition type dodecapoles. An electromagnetic electrode 22 that constitutes the dodecapole is made up of a Permalloy. As materials of the electromagnetic electrode 22, soft magnetic metal such as pure iron and permendurs, in addition to Permalloys, can be used. As materials of the support base, a material of alumina was used.

The support base 5 and the ceramic prop 2 are shown by oblique lines in FIG. 3 to indicate that they are insulator materials. A grounded shield metal 23 is fitted into the inside of the support base 5 in order to prevent charge up. This serves as a cover so that the beam may not see the insulator material directly as less as possible.

Voltage impression at the electrode 21 is done from a power supply 343 (see FIG. 4) outside the vacuum by inserting lead wire of a feedthrough 29 into a hole at the end of the electrode and fixing it with fixed screw or by pressing a contactor with a pressing spring. The Permalloy electrode 22 is connected to the coil outside the vacuum via the shaft 25 of a soft magnetic material, and generates a magnetic field from the top of the magnetic pole by a current being flowed in a coil 28 from the power supply 343 (see FIG. 4). At the same time, by impressing a voltage from the power supply 343 to the Permalloy electrode 22, it is made to act as an electromagnetic electrode. A magnetic yoke 26 for forming a magnetic circuit is connected with the end of the shaft via an insulation sleeve 27.

The chromatic aberration correction is performed by exciting an electric quadrupole field in the first, second, third, and fourth stages, and at the same time by exciting a magnetic quadrupole field shifted in phase from the electric quadrupole field by 45° in the second and third stages. The spherical aberration correction is performed by exciting an electric octapole field in the first, second, third, and fourth stages. Since in actual correction, the each multipole cannot be aligned to the optical axis mechanically in the order of nanometer, the two-electrode fields (each acting as a deflector) are excited in the respective stages and are superimposed with the electric field of the multipoles, and the dipole fields are adjusted so that the beam may passes through the center of the electric quadrupole field in each stage. Moreover, a hexapole field is excited in each stage to correct threefold astigmatism and on-axis coma aberration.

In order to avoid a drift due to heat generation of the coil in a vacuum, this corrector adopts a configuration where the coil 28 is disposed out of the vacuum. Therefore, a case of a corrector 24 needs to be a non-magnetic metal, and a Permalloy shield 25 is provided for shielding an external magnetic field, so that the magnetic field shield may not be broken between the upper part and the lower part of the corrector. In FIG. 3, the Permalloy shield 25 is single. If the shield is provided to be twofold or threefold, the aberration corrector is made less responsive to disturbance magnetic field noise.

As in the above, the aberration corrector of this embodiment each of whose multipoles is constructed with a brazed electrode combination have various advantages compared to the aberration corrector constructed with multipole of the conventional configuration, and especially makes realizable the aberration corrector suited to mass production. Moreover, since the magnetic field is concentrated to the tip efficiently, the characteristics themselves of the aberration corrector are improved.

Incidentally, for the convenience of explanation, in this embodiment, the configuration example of the multistage multipole of the four-stage dodecapole was explained. It is natural that the configuration of this embodiment can also be applied to other multipoles than the dodecapole, such as the hexapole and the octapole. Moreover, the configuration of this embodiment can be applied to the multistage multipole such that the multipoles are accumulated for more than four stages. In addition, if the material of the electrode or magnetic pole is changed for the use of the electrode and for the use of the magnetic pole, it is possible to configure the multipole that are different in their property freely, i.e., the electric field type multipole, the magnetic field type multi-magnetic pole, the electromagnetic field type multipole.

Second Embodiment

This embodiment will explain an embodiment where the aberration corrector shown by the first embodiment is applied to a field emission SEM (FE-SEM), as an application example to a charged particle beam apparatus.

Figure 4:
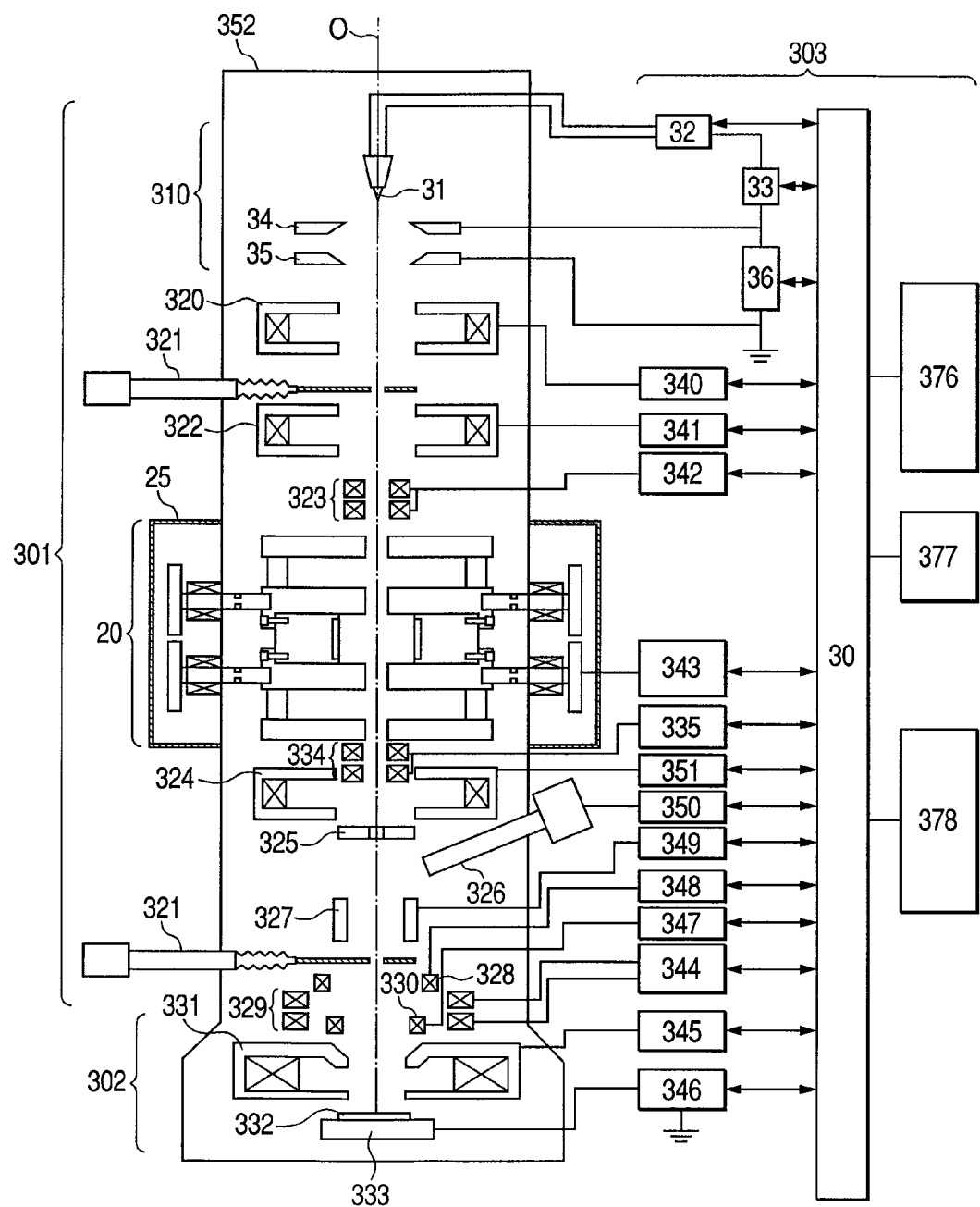
FIG. 4 is an outline configuration of an FE-SEM to which the present invention is applied.

FIG. 4 shows a configuration example of the FE-SEM equipped with the aberration corrector that uses a brazed multistage multipole. This SEM is constructed with an SEM column 301 for irradiating or scanning an electron beam on a specimen, a specimen chamber 302 for housing the specimen stage, a controller 303 for controlling constituent parts of the SEM column 301 and the specimen chamber 302, etc. In FIG. 4, illustrations and explanations of an ion pump, a turbo molecular pump, vacuum piping, and a vacuum system control mechanism are omitted. The controller 303 is further connected with a data storage 376 for storing predetermined pieces of information, a monitor 377 for displaying an acquired image, an operation console 378 serving as a man-machine interface between the apparatus and an apparatus user. The operation console 378 includes information input means, for example, a keyboard, a mouse, etc.

First, components inside the SEM column 301 will be explained. A field emitter 31 is an electron source that is a single crystal of tungsten whose tip is sharpened by electropolishing, and makes electric field emission electrons emit by cleaning the surface of the single crystal through electrification-heating by a flashing power supply 32, and impressing a voltage of about +5 kV between the single crystal and an extraction electrode 34 using an extraction power supply 33 in a ultra high vacuum in the order of $10^{-8}$ Pa. The electrons that are accelerated and converged by an electrostatic lens formed between the extracting electrode 34 and a second anode 35 enter into a component in a later stage along the optical axis 0. The electrons are converged by a first condenser lens 320, and the amount of the beam is limited by a movable aperture 321. The electrons pass through a second condenser lens 322 and a double deflector 323, and enter into an aberration corrector 20. The double deflector 323 is adjusted so that the axes of a field emission gun 310 and the condenser lenses 320, 322 may agree with the axis of the aberration corrector 20. The beam coming out of the aberration corrector 20 is adjusted by a double deflector 334 so that its axis may agree with the optical axis of a lens 324 and an objective lens 331.

Next, operations of the aberration corrector will be explained. The aberration corrector 20 of this embodiment is a four-electrode and eight-electrode system aberration corrector and is capable of correcting the chromatic aberration and the spherical aberration. The four-electrode and eight-electrode are formed in each stage of the aberration corrector 20. If a 12-electrode (this may act as a magnetic pole) is used for them, two-electrode, six-electrode, and 12-electrode can also be formed in superposition, in addition to the four-electrode and the eight-electrode. These multipole fields are used in order to correct parasitic aberration that is caused by errors in assembly of the electrodes and magnetic poles and ununiformity of the magnetic pole material, for example, the on-axis coma aberration, the threefold astigmatism, fourfold astigmatism, etc.

The electron beam adjusted in terms of an angle that accords to the amount of off-axis as much as canceling mainly the chromatic aberration and the spherical aberration of the objective lens 331 by the aberration corrector 20 is once focused in the vicinity of an E×B deflector 327 by the lens 324. Forming a crossover in the vicinity of the E×B deflector is to lessen an influence of the aberration of the E×B deflector 327. Moreover, the lens 324 also suppresses the increase of fourth-order chromatic and spherical combination aberration and the fifth-order spherical aberration after correction of the chromatic aberration and the spherical aberration. Therefore, in order to acquire a high-resolution image by aberration correction, the lens 324 is needed. Then, the electron beam is focused onto a specimen 332 by the objective lens 331, and is scanned on the specimen by a scanning deflector 329. A leader line numeral 328 designates a beam aligner.

Inside the specimen chamber 302, a specimen stage 333 equipped with a specimen mounting plane on which the specimen 332 is placed and held is housed. The secondary charged particles (in this case, secondary electrons or backscattered electrons) generated by electron beam irradiation pass through the objective lens 331, hit a reflection plate 325, and generate secondary particles. The generated electrons are detected by a secondary electron detector 326. The E×B deflector 327 directly guides the secondary electrons to the secondary electron detector 326 by bending trajectories of the secondary electrons generated from the specimen, or adjusts a position of the reflection plate 325 on which the secondary electrons generated from the specimen hit, and improves the detection efficiency. The detected secondary electron signal is taken into a computer 30 as a luminance signal synchronizing with the scan. The computer 30 performs proper processing on the taken-in luminance signal information, and displays it on the monitor 377 as an SEM image. Although only one detector is shown here, plural detectors can be arranged so that an image can be acquired while selecting energy or an angle distribution of the reflected electrons and the secondary electrons. If a secondary electron detector in the form of a coaxial disc with a hole in its center is disposed on the optical axis 0, the reflection plate 325 is not necessarily required.

The controller 303 is constructed with the flashing power supply 32, an extraction power supply 33, an acceleration power supply 36, a lens current supply 340, a lens current supply 341, a current supply 351, a power supply 342, the power supply 343, a current supply 344, an objective lens current supply 345, a retarding voltage power supply 346, a stigmator power supply 347, a beam aligner power supply 348, an E×B beam deflector power supply 349, a secondary electron detection power supply 350, etc., each of which is connected with a corresponding component in the SEM column by a signal transmission passage, electric wiring, etc.

According to the present invention, since the assembly of the aberration corrector is more simplified than before and attains higher accuracy, the difference in performance among SEM's that use this becomes smaller, which makes easier the adjustment and improves the productivity in mass production. Regarding the aberration corrector itself, an increase in the assembly accuracy decreases the amount of parasitic aberration and improves the performance. By having restricted the magnetic pole tip angle, a magnetic field leaking from the side faces to the adjacent electrode decreases and the magnetic field concentrates to the tip of the pole. Since generation efficiencies of various multipole fields increase thereby, the capacity of a current source is allowed to be small and the generation of parasitic aberration is suppressed; therefore, correction performance is improved.

Incidentally, although in this embodiment, a configuration example of the scanning electron microscope equipped with an aberration corrector of the four-stage 12-electrode such that the first stage and the fourth stage are the electric field type multipole, and the second stage and the third stage are the electromagnetic field superposition type multipole was explained, the aberration corrector may be configured to have the magnetic field type multipole for the first stage and the fourth stage. In this case, since the power supply for supplying magnetizing current to the magnetic field type multi-magnetic pole and the electromagnetic field superposition type multipole can be common, there is an advantage that the number of voltage sources that easily act as noise sources can be reduced below that of the aberration corrector whose configuration is shown in FIGS. 2(A) and 2(B).

Third Embodiment

Figure 5:
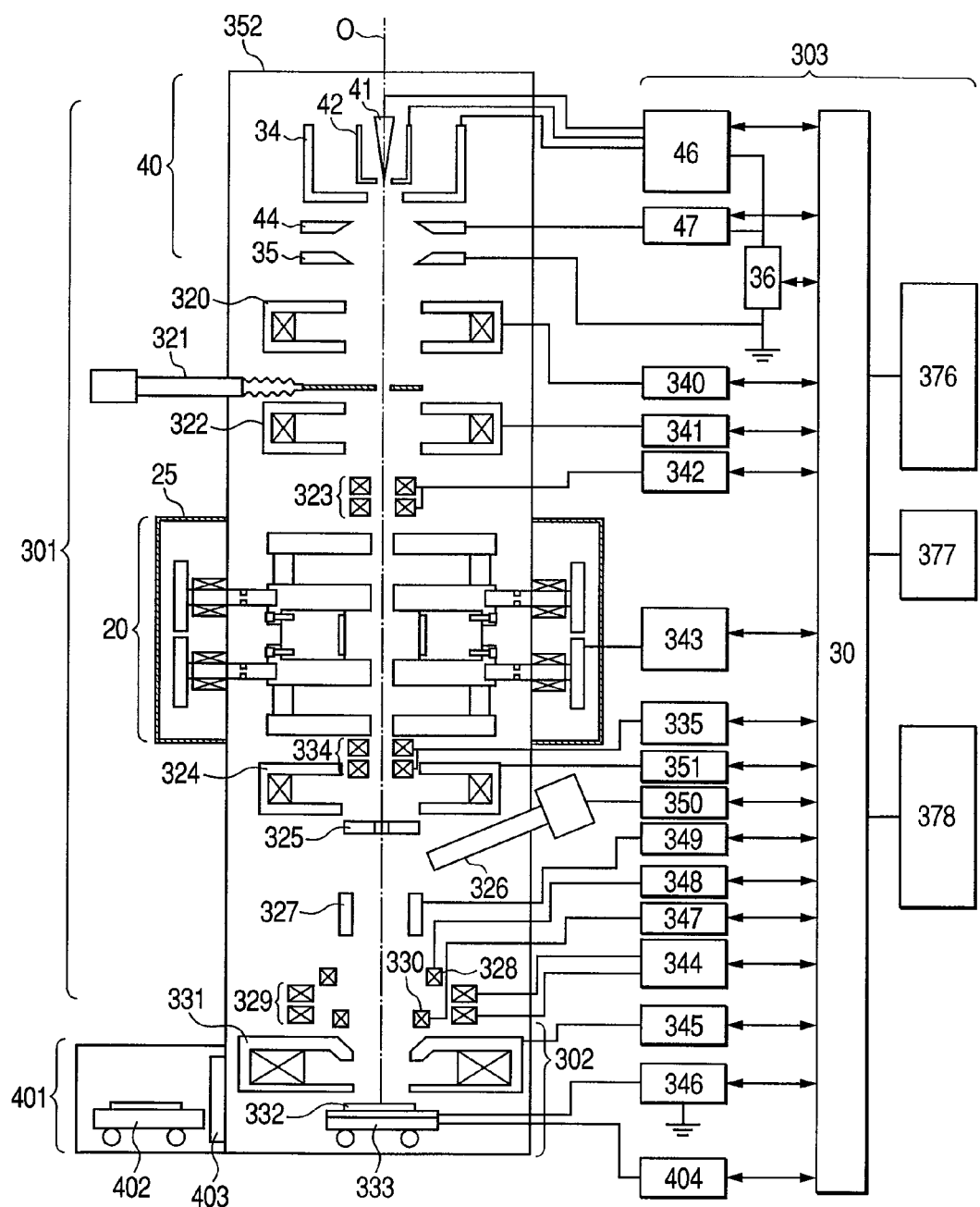
FIG. 5 is an outline configuration of a critical dimension SEM to which the present invention is applied.

FIG. 5 shows a configuration example of a critical dimension SEM (CD-SEM) equipped with the aberration corrector that uses a brazed multistage multipole. Since the configuration shown in FIG. 5 has many common parts to those of the configuration in FIG. 4, only parts that have different structures will be explained. In this embodiment, a Schottky emission gun 40 is used. A Schottky emitter 41 is an electron source that is made of tungsten single crystal into which oxygen, zirconium, etc. are diffused and uses the Schottky effect. In its vicinity, a suppressor electrode 42 and an extraction electrode 34 are provided. Schottky electrons are made to emit by heating the Schottky electron source 41 and impressing a voltage of about +2 kV at the extraction electrode 34. A negative voltage is impressed at the suppressor electrode 42 to suppress electron emission from any location of the Schottky electron source 41 other than its tip. Although an energy width and a light source diameter become large compared to the field emission electron gun, a large probe current can be taken, no flashing is necessary, and it is suitable for continuous running.

Since the CD-SEM of this embodiment measures a resist pattern on a semiconductor wafer etc., normally it is used with landing energy held down to 1 keV or less from the viewpoint of specimen damage control. In the CD-SEM, the working distance is constant. Working conditions of the aberration corrector corresponding to several observation modes each having different landing energy, retarding voltage values, etc. are stored in the data storage 376. Upon selection by the operator, the computer 30 calls selected working conditions, sets each power supply to the conditions, and then performs the observation mode. The specimen chamber 302 is provided with a preparation chamber 401 for carrying a wafer into the specimen chamber 302. The wafer specimen is passed through a gate valve 403, and is set on the specimen stage 333 therein by a specimen carrier 402. For measurement locations that were inputted in advance, the computer 30 performs the following operations automatically: moving the stage by controlling a specimen stage controller 404; focusing with the objective lens 331; correcting astigmatic aberration using an astigmatic correction coil 330; and measuring a critical dimension, recording data, acquiring an image, storing the data, etc. by controlling the scanning deflector 329, the secondary electron detector 326, etc.

Fourth Embodiment

It is also possible to construct a focused ion beam system (FIB) by using the multistage multipole explained in FIGS. 1(A) to 1(E). A component provided in the charged particle optical column for FIB is an ion gun instead of the electron gun. Its condenser lens and objective lens are each made up of an electrostatic lens. The components thereof are much the same as the components of the optical column for electron beam except a point that the deflector is of an electric field type. There is also a case where a secondary electron detector for detecting secondary electrons generated by ion beam irradiation may be provided in the charged particle optical column for FIB system. However, when considering the multipole to be used in the aberration corrector for FIB, there is two problems: an ion trajectory is hard for the magnetic field to bend because of large mass of the ion, and since a beam includes an isotope with a different mass, the trajectory may be split because of a difference of mass with the magnetic pole. Therefore, the electrode must be used for all poles. Therefore, the aberration corrector for FIB system has a configuration where the electrodes 1, 2, 3, and 4 shown in FIGS. 2A and 2B are each made up of a non-magnetic metal, and the feedthrough 29 is connected to a rear part of the electrode instead of the shaft 25 and the magnetic yoke 26 of a soft magnetic material shown in FIG. 3, and corrects only the spherical aberration. Since the aberration corrector corrects the spherical aberration, beam flare is lessened, which enables the FIB system to perform fast and high-precision machining. The focused ion beam system of this embodiment realizes a focused ion beam system capable of high-precision machining or image observation.

Fifth Embodiment

Figure 7:
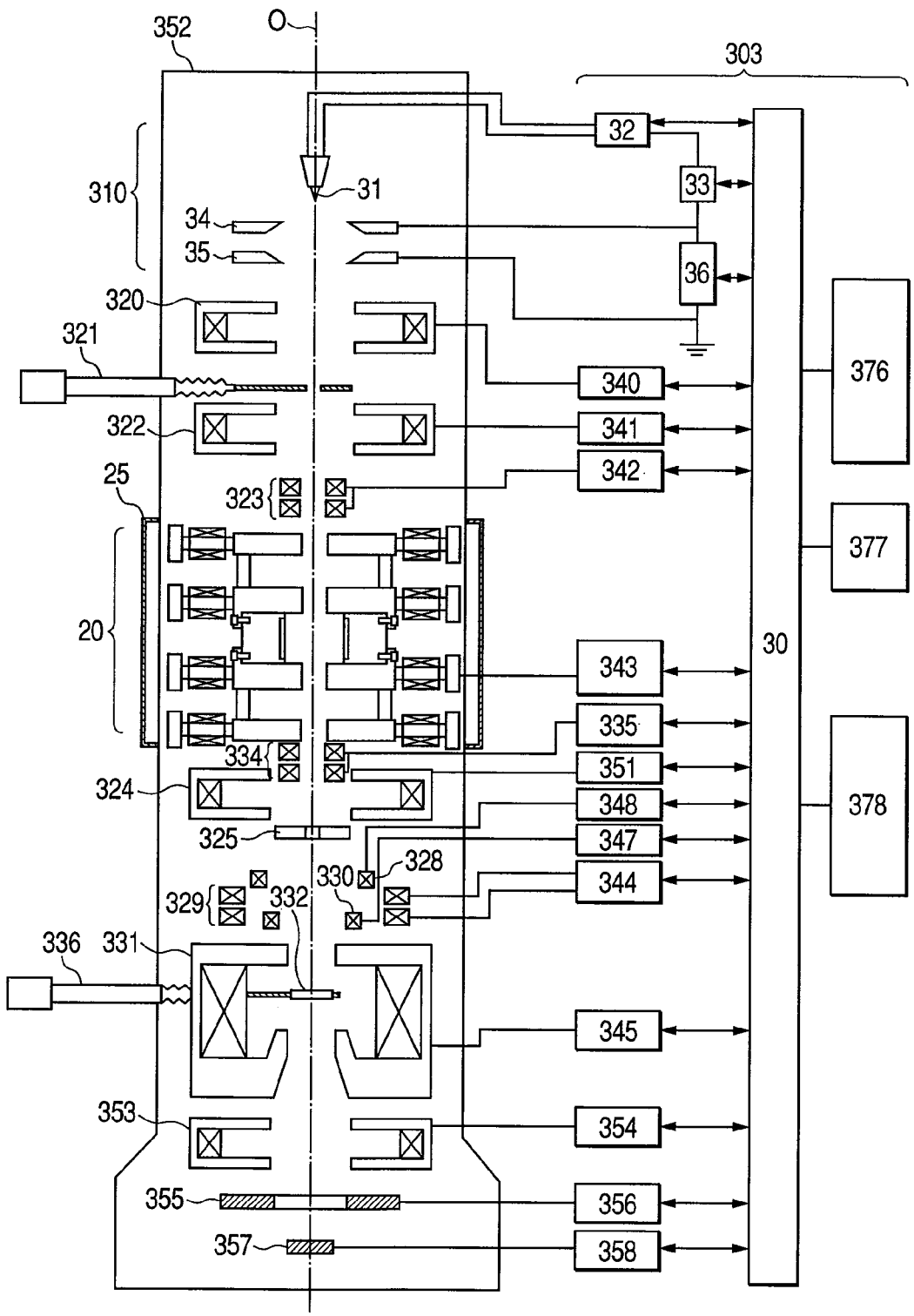
FIG. 7 is an outline configuration of STEM to which the present invention is applied.

FIG. 7 shows an example of constructing the scanning transmission electron microscope (STEM) using the multistage multipole explained in FIGS. 1(A) to 1(E). The charged particle optical column for STEM is constructed with: the field emission gun 310 for generating an electron beam and emitting it by a predetermined acceleration voltage; the scanning deflector 329 for scanning the electron beam on the specimen; the objective lens 331 for focusing and irradiating the electron beam on the specimen; an annular detector 355 for detecting the electron beam penetrating the specimen; an axis detector 357; etc. Since the transmission electrons must be detected, the specimen for STEM needs to be thinned; it is disposed on the optical axis 0 of the electron beam by a side entry specimen holder 336 etc. in a state of being fixed to a mesh.

In the STEM of a high acceleration voltage, resolution is mainly restricted not by the chromatic aberration but by the spherical aberration. In the case of correcting only the spherical aberration, it is not necessary to use the electromagnetic superposition electrode, and so the magnetic field type multi-magnetic poles are used altogether. The spherical aberration corrector for STEM is disposed, for example, between the electron gun and the objective lens. The aberration corrector 20 of this embodiment is constructed with the four-stage 12-electrode multi-magnetic pole that uses the magnetic field type multi-magnetic poles altogether. In the case where the four-electrode and the eight-electrode are not superposed but set to be independent, the aberration corrector 20 can be constructed with seven stages of the magnetic poles at minimum. In the aberration corrector of this construction, in the case of the electric field type multipole, noise ranging from a low frequency of a few Hz to a high frequency of an order of GHz affects the beam, whereas in the case of the magnetic field type multi-magnetic pole, the coil does not respond to such a fast electric noise, and accordingly the power supply noise causes less influence than in the electric field type multipole.

Sixth Embodiment

Figure 6:
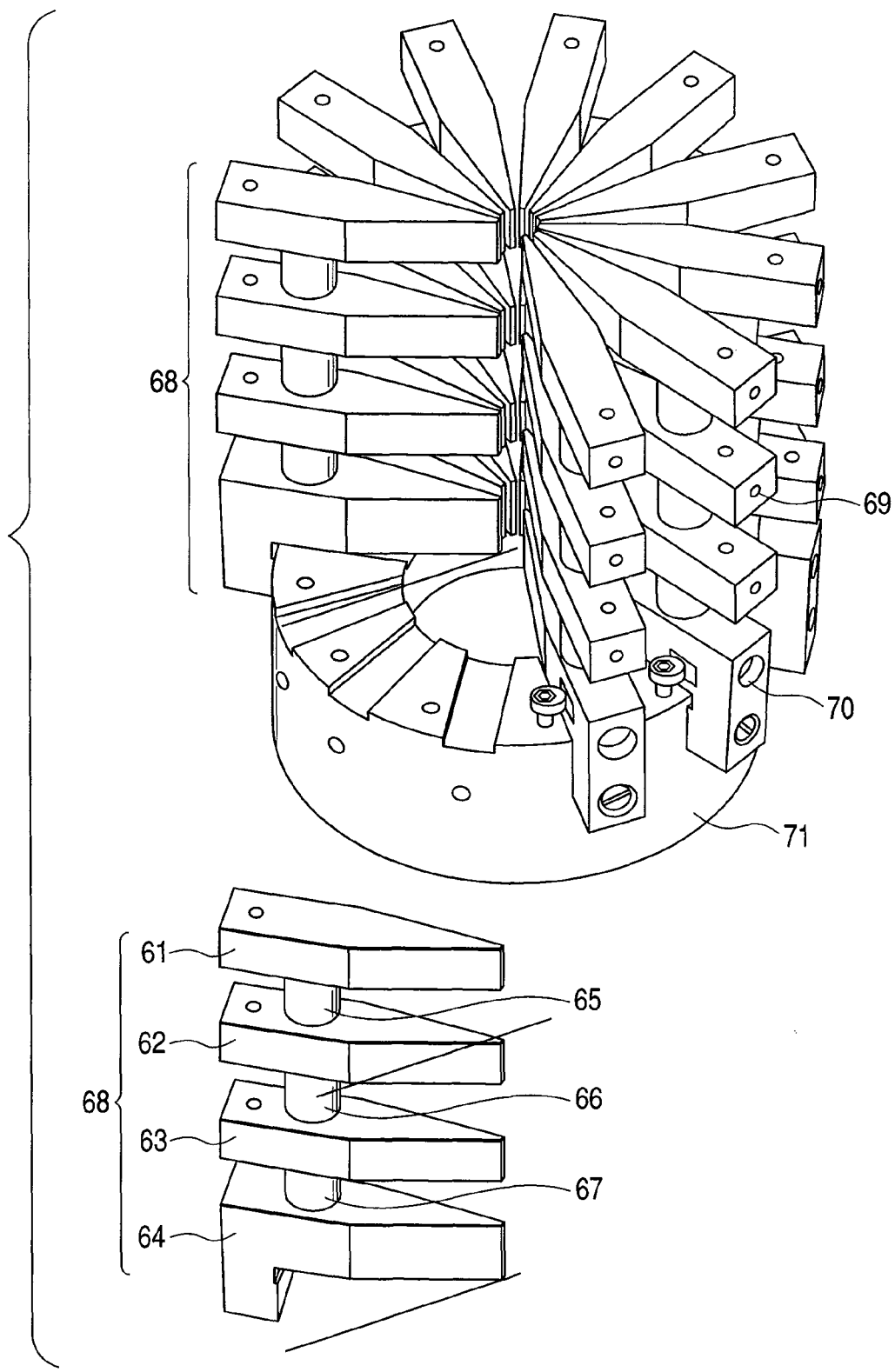
FIG. 6 is a configuration of the aberration corrector using a four-stage multipole element.

In this embodiment, an embodiment of a four-stage multipole of a configuration shown in FIG. 1(D) will be explained. FIG. 6 shows a configuration of a four-stage electromagnetic field superposition type dodecapole that uses the four-stage multipole element. Since the configuration of the multipole shown in FIG. 6 has many common parts to those of the multipole shown in FIGS. 2(A) and 2(B), explanations of the common parts are omitted as much as possible.

First, electrodes or magnetic poles 61 to 63 are manufactured by grinding processing of a block of a titanium material. An installation hole 69 for voltage introduction is drilled on the rear side of the electrodes 61 to 63. Similarly, an electromagnetic electrode or magnetic pole 64 is manufactured by grinding processing of a Permalloy block. A screw hole 70 for allowing fitting-in of the soft magnetic shaft that constitutes a magnetic circuit has been opened. These electrodes or magnetic poles 61 to 64 are bonded to a ceramic prop, such as of alumina, respectively. The bonding is done by brazing using a silver braze similarly with the first embodiment.

After the completion of the brazing, the four-stage electrode piece is subjected to polishing processing to expose the side faces. The multipole element after the completion of the finish machining is attached to a support base 71 in the similar manner as the first embodiment to complete the four-stage 12-electrode. Since the multipole shown in FIG. 6 already has the four-stage multipole, it can operate as the aberration corrector for correcting the chromatic aberration and the spherical aberration without appending an additional multipole.

The dodecapole using the four-stage multipole element of this embodiment has smaller number of times of attachment to the support base than that of the first embodiment. Moreover, since the number of times of finish machining of the multipole element allows to be lessened, the assembly process of the aberration corrector is simplified compared to that of the configuration of the aberration corrector of the first embodiment. Still moreover, the four-stage multipole element of this embodiment is advantageous especially when constructing a multistage multipole having an extremely large number of stages, such as eight stages, 10 stages, or 19 stages. For example, if groove machining is performed on the rear face of the support base and the four-stage multipole element is attached thereto, the aberration corrector of the eight-stage multipole can be constructed; if the support base is attached to the eight-stage multipole, and further the two-stage multipole is attached thereto, a 10-stage multipole can be realized. Furthermore, if the four-stage multipole is accumulated by four times and a three-stage multipole including a three-multipole element is accumulated thereon, 19-stage multipole will be realizable.

Incidentally, regarding the number of stages of the multipole element, if the number of stages is made too large, there is a case where sufficient bonding strength cannot be obtained, the number of stages should be increased as much as possible within a limit where sufficient bonding strength is obtainable. The multistage multipole of an arbitrary number of stages is manufactured by accumulating the multipole of the maximum number of stages obtained to an integral multiple and accumulating thereon other multipole so as to make up a deficiency of the number of stages.

The present invention can be used for the aberration corrector, the electron energy-loss spectrometer, and apparatuses and systems that are equipped with them, such as the scanning electron microscope, the semiconductor inspection apparatus, the scanning transmission electron microscope, the transmission electron microscope, and the focused ion beam system.

What is claimed is:

1. An aberration corrector, having a multipole element member that a first electrode and a second electrode both being made up of a metal material are integrated into a single piece by brazing the electrodes so as to sandwich a ceramic material in a vertical direction, and
   a support base that has an aperture part allowing a charged particle beam to pass through in its center part and is for fixing the plurality of multipole element members,
   wherein multistage multipoles constructed by fixing the plurality of multipole element members around the aperture part is used.

2. The aberration corrector according to claim 1,
   wherein the multistage multipole is an electromagnetic field superposition type multipole that is constructed by using an electrode made up of a non-magnetic metal as the first electrode and using a magnetic pole made up of a soft magnetic metal as the second electrode.

3. The aberration corrector according to claim 1,
   wherein the multistage multipole is an electric field type multipole each of which is constructed by using an electrode made up of a non-magnetic metal as the first electrode and as the second electrode.

4. The aberration corrector according to claim 1,
   wherein the multistage multipole is magnetic field type multipole each of which is constructed by using a magnetic pole that includes the first electrode and the second electrode each being made up of a soft magnetic metal.

5. The aberration corrector according to claim 2,
   wherein the non-magnetic metal is made up of a titanium material.

6. The aberration corrector according to claim 3,
   wherein the non-magnetic metal is made up of a titanium material.

7. The aberration corrector according to claim 2,
   wherein the soft magnetic metal is any one of a Permalloy, pure iron, and a permendur.

8. The aberration corrector according to claim 4,
   wherein the soft magnetic metal is any one of a Permalloy, pure iron, and a permendur.

9. The aberration corrector according to claim 1,
   wherein a groove to which the multipole element member fits is formed on the surface of the support base, and one sidewall of the groove serves as a base level where the multipole element member is aligned.

10. The aberration corrector according to claim 1,
    wherein tip shapes of the first electrode and the second electrode are wedges, and angles of the wedge-shaped tips range from 15° to 25°.

11. A charged particle beam apparatus that has a specimen stage on which a specimen is placed and held, and a charged particle beam optical system equipped with a function of irradiating a primary charged particle beam on the specimen, detecting secondary charged particles generated by the irradiation, and outputting a signal,
    wherein the charged particle beam optical system is equipped with lens means for deflecting or converging the charged particle beam and an aberration corrector for correcting aberration generated by the lens means, and
    the aberration corrector has a multipole element member that is integrated into a single piece by brazing a first electrode and a second electrode made up of a metal material in a vertical direction with a ceramic material interposed therebetween, and a support base that has an aperture part allowing the charged particle beam to pass through in its central part and is for fixing the plurality of multipole element members, and has a multistage multipole constructed by fixing the plurality of multipole element members around the aperture part.

12. The charged particle beam apparatus according to claim 11,
    wherein the charged particle optical system is equipped with an electron gun for generating an electron beam and a scanning deflector for scanning the charged particle beam on the specimen,
    the aberration corrector has a four-stage multipole constructed by fixing a plurality of multipole element members to the both sides of the support base, and
    the multipole that is near to the support base among the four-stage multipoles is an electromagnetic field superposition type multipole.

13. The charged particle beam apparatus according to claim 12,
    wherein all the multipoles other than the electromagnetic superposition type multipole among a plurality of multipoles that constitute the four-stage multipole are magnetic field type multipole.

14. The charged particle beam apparatus according to claim 11,
    wherein the charged particle optical system is equipped with an ion gun for generating an ion beam, and
    the aberration corrector is constructed with only an electric field type multipole such that the first electrode and the second electrode are all made up of a non-magnetic material.

15. The charged particle beam apparatus according to claim 11,
    wherein the aberration corrector is equipped with a structure where a plurality of the multistage multipoles are further accumulated.

16. A scanning electron microscope that has a specimen mount on which a specimen is placed and held, and an electron optics column equipped with a function that irradiates an electron beam on the specimens, detects secondary electrons or reflected electrons generated by the irradiation, and outputs a signal,
    wherein the electron optics column is equipped with lens means for deflecting or converging the electron beam and an aberration corrector for correcting aberration generated by the lens means, and
    the aberration corrector is equipped with a multipole element member that integrates a first electrode and a second electrode made up of a metal material in a vertical direction with a medium of a ceramic material by brazing and a support base that has an aperture part allowing the electron beam to pass through its central part and is for fixing the plurality of multipole element member, and is equipped with multistage multipole each of which is constructed by fixing the plurality of multipole element members around the aperture part.

* * * * *